United States Patent [19]

Seele et al.

[11] Patent Number: 5,017,594
[45] Date of Patent: May 21, 1991

[54] 1-HALO-1-AZOLYLPROPENES AND -METHYLOXIRANES AND FUNGICIDES CONTAINING THESE COMPOUNDS

[75] Inventors: Rainer Seele; Reiner Kober, both of Fussgoenheim; Norbert Goetz, Worms; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 376,429

[22] Filed: Jul. 7, 1989

[30] Foreign Application Priority Data

Jul. 29, 1988 [DE] Fed. Rep. of Germany ....... 3825841

[51] Int. Cl.$^5$ ................. A01N 43/653; C07D 249/08
[52] U.S. Cl. ..................................... 514/383; 514/184; 548/101; 548/268.8
[58] Field of Search ..................... 548/101, 262, 268.8; 514/184, 383

[56] References Cited

U.S. PATENT DOCUMENTS

| | | | |
|---|---|---|---|
| 4,104,399 | 8/1978 | Pommer et al. | 514/383 |
| 4,213,990 | 7/1980 | Frick et al. | 514/383 |
| 4,255,434 | 3/1981 | Kramer et al. | 548/262 |
| 4,464,381 | 8/1984 | Janssen et al. | 514/383 |
| 4,495,191 | 1/1985 | Ehrhardt et al. | 514/383 |
| 4,652,580 | 3/1987 | Janssen et al. | 514/383 |
| 4,657,921 | 4/1987 | Frick et al. | 514/383 |
| 4,740,515 | 4/1988 | Weissmuller et al. | 514/383 |
| 4,758,670 | 9/1988 | Muller et al. | 548/262 |

FOREIGN PATENT DOCUMENTS

| | | | |
|---|---|---|---|
| 1257276 | 7/1989 | Canada . | |
| 118245 | 9/1984 | European Pat. Off. | 548/262 |

*Primary Examiner*—Glennon H. Hollrah
*Assistant Examiner*—Patricia L. Morris
*Attorney, Agent, or Firm*—Oblon, Spivak, McClelland, Maier & Neustadt

[57] ABSTRACT

1-Halo-1-azolylpropenes and -methyloxiranes of the formula I

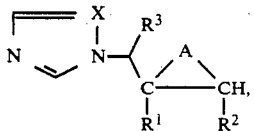

where $R^1$ and $R^2$ are alkyl, cycloalkyl, cycloalkenyl, tetrahydropyranyl, norbornyl, pyridyl, naphthyl, biphenyl or phenyl, A is oxygen or a single bond, $R^3$ is F, Cl or Br, X is CH or N, their plant-tolerated acid addition salts and metal complexes, and fungicides containing these compounds.

6 Claims, No Drawings

1-HALO-1-AZOLYLPROPENES AND -METHYLOXIRANES AND FUNGICIDES CONTAINING THESE COMPOUNDS

The present invention relates to novel azole compounds, processes for their preparation, fungicides which contain these compounds and methods for controlling fungi.

It is known that triazolylmethyloxiranes, for example 2-(1,2,4-triazol-1-ylmethyl)-2-phenyl-3-(4-chlorophenyl)-oxirane or 2-(imidazol-1-ylmethyl)-2-phenyl-3-(4-chlorophenyl)-oxirane (DE-32 18 130.2), can be used as fungicides. However, the fungicidal actions are unsatisfactory.

We have found that 1-halo-1-azolylpropenes and -methyloxiranes of the formula I

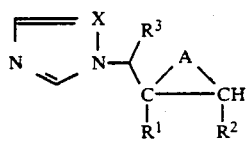

where $R^1$ and $R^2$ are identical or different and are each $C_1$-$C_8$-alkyl, $C_5$-$C_8$-cycloalkyl, $C_5$-$C_8$-cycloalkenyl, tetrahydropyranyl, norbornyl, pyridyl, naphthyl, biphenyl or phenyl, and these radicals may be monosubstituted to trisubstituted by halogen, nitro, phenoxy, amino, alkyl, alkoxy or haloalkyl, each of 1 to 4 carbon atoms, A is O or a single bond, $R^3$ is F, Cl or Br and X is CH or N, and their plant-tolerated acid addition salts and metal complexes, have a better fungicidal action than known azole compounds.

The compounds of the formula I contain asymmetric carbon atoms and can therefore occur as enantiomers and diastereomers. In the case of the novel compounds, the mixtures of diastereomers can be separated in a conventional manner, for example on the basis of their different solubilities or by column chromatography, and can be isolated in pure form. The racemates of the novel compounds can be resolved by a known method, for example by salt formation with an optically active acid, separation of the diastereomeric salts and liberation of the enantiomers by means of a base. Both the pure diastereomers or enantiomers and the mixtures of these obtained in the synthesis can be used as fungicides.

$R^1$ and $R^2$ are each, for example, $C_1$-$C_8$-alkyl, in particular $C_1$-$C_4$-alkyl (methyl, ethyl, isopropyl, n-propyl, n-butyl, sec-butyl, tert-butyl, n-pentyl or neopentyl), 1-naphthyl, 2-naphthyl, p-biphenyl, phenyl, halophenyl (2-chlorophenyl, 2-fluorophenyl, 2-bromophenyl, 3-chlorophenyl, 3-bromophenyl, 3-fluorophenyl, 4-fluorophenyl, 4-chlorophenyl, 4-bromophenyl, 2,4-dichlorophenyl, 2,3-dichlorophenyl, 2,5-dichlorophenyl, 2,6-dichlorophenyl, 2-chloro-6-fluorophenyl or 2-chloro-4-fluorophenyl), $C_1$-$C_4$-alkoxyphenyl (2-methoxyphenyl, 3-methoxyphenyl, 4-methoxyphenyl, 2,4-dimethoxyphenyl, 4-tert-butoxyphenyl or 3,4-dimethoxyphenyl), $C_1$-$C_4$-alkylphenyl (4-ethylphenyl, 4-isopropylphenyl or 4-tert-butylphenyl), 2-chloro-6-methylphenyl, 3-phenoxyphenyl, 4-phenoxyphenyl, 3-nitrophenyl, 4-nitrophenyl, 3-aminophenyl, 4-aminophenyl, 2-aminophenyl, 2-trifluoromethylphenyl, 3-trifluoromethylphenyl,4-trifluoromethylphenyl, 3-pyridyl, tetrahydropyranyl, cyclopropyl, cyclopentyl, cyclohexyl, 2-cyclohexenyl, 3-cyclohexenyl or norbornyl.

Examples of acid addition salts are the hydrochlorides, hydrobromides, sulfates, nitrates, phosphates, oxalates and dodecylbenzenesulfonates. The activity of the salts is due to the cation, and in general the anion is therefore unimportant. The novel active ingredient salts are prepared by reacting an imidazolylmethyloxirane (I) with an acid.

Metal complexes of the active ingredients I or of their salts can be formed, for example, with copper, zinc, tin, manganese, iron, cobalt or nickel, by reacting an imidazolylmethyloxirane with an appropriate metal salt, for example with copper sulfate, zinc chloride, tin chloride or manganese sulfate.

The compounds of the formula I in which A is O and $R^3$ is F, Cl or Br can be prepared, for example, by reacting a compound of the formula II

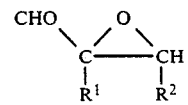

where $R^1$ and $R^2$ have the stated meanings, with a compound of the formula III

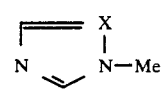

where Me and X have the abovementioned meanings, in the presence of a thionyl halide.

The reaction is carried out, for example, in the presence or absence of a solvent or diluent at from −30 to 80° C. The preferred solvents and diluents include nitriles, such as acetonitrile or propionitrile, ethers, such as tetrahydrofuran, diethyl ether, dimethoxyethane, dioxane or diisopropyl ether, and in particular hydrocarbons and chlorohydrocarbons, such as pentane, hexane, toluene, methylene chloride, chloroform, carbon tetrachloride or dichloroethane, or mixtures of these.

The novel starting compounds II are obtained, for example, by epoxidation of the corresponding olefins IV

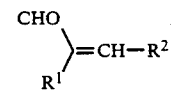

where $R^1$ and $R^2$ have the abovementioned meanings, with a peroxycarboxylic acid, such as perbenzoic acid, 3-chloroperbenzoic acid, 4-nitroperbenzoic acid, monoperphthalic acid, peracetic acid, perpropionic acid, permaleic acid, monopersuccinic acid, perpelargonic acid or trifluoroperacetic acid, in an inert solvent, preferably a chlorohydrocarbon, eg. methylene chloride, chloroform, carbon tetrachloride or dichloroethane, or, if necessary, in acetic acid, ethyl acetate, acetone or dimethylformamide, in the presence or absence f a buffer, such as sodium acetate, sodium carbonate, disodium hydrogen phosphate or Triton B. The reaction is carried out at, for example, from 10° to 100° C. and, if necessary, is catalyzed with, for example, iodine, sodium tungstate or light. Suitable oxidizing agents also include alkaline solutions of hydrogen peroxide (about 30% strength) in methanol, ethanol, acetone or acetonitrile at from 25° to 30° C., and alkyl hydroperoxides, eg. tert-butyl hydroperoxide, with the addition of a catalyst, eg. sodium tungstate, pertungstic acid, molybdenum hexacarbonyl or vanadyl acetylacetonate. Some of the stated oxidizing agents can be prepared in situ.

The compounds of the formula I in which A is a single bond can be prepared, for example, by reacting a compound of the formula IV

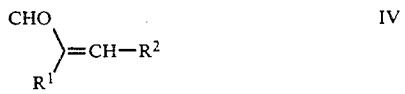

where $R^1$ and $R^2$ have the abovementioned meanings, with a compound of the formula III

where Me and X have the abovementioned meanings in the presence of a thionyl halide.

The reaction is carried out, for example, in the presence or absence of a solvent or diluent at from $-30°$ to 80° C. The preferred solvents and diluents include nitriles, such as acetonitrile or propionitrile, ethers, such as tetrahydrofuran, diethyl ether, dimethoxyethane, dioxane or diisopropyl ether, and in particular hydrocarbons and chlorohydrocarbons, such as pentane, hexane, toluene, methylene chloride, chloroform, carbon tetrachloride or dichloroethane, or mixtures of these.

The compounds IV can be prepared by generally known methods of aldehyde synthesis (Houben-Weyl-Müller, Methoden der Organischen Chemie, Georg Thieme Verlag, Stuttgart 1983, Vol. E 3).

The Examples which follow illustrate the preparation of the active ingredients.

1. Preparation of the starting materials

Method 1

E/Z-2-(4-fluorophenyl)-3-(2-chlorophenyl)-propenal 4.2 g of sodium hydroxide in 30 ml of water are added to a solution of 35 g of 2-chlorobenzaldehyde in 300 ml of methanol. The reaction mixture is cooled to 10° C. and 36 g of 4-fluorophenylacetaldehyde are added rapidly, the temperature of the solution increasing to 30°–40° C. The mixture is stirred for 10 hours at 40° C., after which the precipitated crystals are filtered off under suction from the cooled reaction solution.

Method 2

Cis-2-formyl-2-(4-fluorophenyl)-3-(2-chlorophenyl)oxirane 78.2 g of E-2-(4-fluorophenyl)-3-(2-chlorophenyl)-propenal are dissolved in 300 ml of methanol, and 1 ml of concentrated sodium hydroxide solution is added. The reaction solution is stirred at 0° C while 20.5 g of hydrogen peroxide (about 50% strength) are slowly added dropwise, the internal temperature not exceeding 30° C. After the end of the addition, stirring is continued for six hours at room temperature (20° C.), after which 100 ml of water are added and the resulting emulsion is extracted by shaking with methyl tert-butyl ether. The isolated organic phase is then dried over sodium sulfate and then evaporated down. 52.5 g (63%) of cis-2-formyl2-(4-fluorophenyl)-3-(2-chlorophenyl)-oxirane are obtained.

Preparation of the end products

EXAMPLE 1

12.8 g of thionyl chloride are added to a solution of 29.7 g of triazole in 150 ml of methylene chloride at 0° C. under a nitrogen atmosphere. After the end of the addition, the mixture is stirred for 30 minutes at room temperature and 20 g of cis-2-formyl-2-(4-fluorophenyl)-3-(2-chlorophenyl)-oxirane are then added. The reaction mixture is stirred for 12–15 hours at room temperature, after which 100 ml of water are added to the solution and the organic phase is separated off. The remaining aqueous phase is extracted twice by shaking with methylene chloride, and the collected organic phases are washed twice with saturated sodium carbonate solution. The isolated organic phase is then dried over sodium sulfate and evaporated down, 23.7 g (85%) of 1'RS-cis-2-[1-(1,2,4-triazol-1-yl)-1-chloromethyl]-2-(4-fluorophenyl)-3-(2-chlorophenyl)-oxirane being obtained as a 2 : 1 diastereomer mixture. 5.8 g of diastereomer A, which is formed in the greater amount and has a melting point of 152°–156° C. (compound no. 1), are obtained from methyl tert-butyl ether.

EXAMPLE 2

27.2 g of thionyl chloride are added to a solution of 63.1 g of triazole in 250 ml of methylene chloride at 0° C. under a nitrogen atmosphere. After the end of the addition, the mixture is stirred for 30 minutes at room temperature and 40 g of E-2-(4-fluorophenyl)-3-(2-chlorophenyl)-propenal are then added. The reaction mixture is stirred for 12–15 hours at room temperature, after which 100 ml of water are added to the solution and the organic phase is separated off. The remaining aqueous phase is extracted twice by shaking with methylene chloride, and the collected organic phases are washed twice with saturated sodium bicarbonate solution. The isolated organic phase is then dried over sodium sulfate and evaporated down, and the residue is purified by chromatography over silica gel (9 : 1 ethyl acetate/n-hexane). 21.7 g (41%) of E-1-chloro-1-(1,2,4-triazol-1-yl)-2-(4-fluorophenyl)-3-(2-chlorophenyl)-prop-2-ene (compound no. 1a) are obtained.

EXAMPLE 3

11.2 g of thionyl bromide are added to a solution of 14.9 g of triazole in 75 ml of methylene chloride at 0° C. under a nitrogen atmosphere. After the end of the addition, the mixture is stirred for 30 minutes at room temperature and 10 g of cis-2-formyl-2-(4-fluorophenyl)3-(2-chlorophenyl)-oxirane are then added. The reaction mixture is stirred for 12–15 hours at room temperature, after which 100 ml of water are added to the solution and the organic phase is separated off. The remaining aqueous phase is extracted twice by shaking with methylene chloride, and the collected organic phases are washed twice with saturated sodium bicarbonate solution. The isolated organic phase is then dried over sodium sulfate and evaporated down, 10.5 g (72%) of 1'RS-cis-2[1-(1,2,4-triazol-1-yl)-1-bromomethyl]-2-(4-fluorophenyl)-3-(2-chlorophenyl)-oxirane being obtained as a 2 : 1 diastereomer mixture. 3.5 g of diastereomer A, which is formed in the greater amount and has a melting point of 151°–155° C. (compound no. 3), are obtained from methyl tert-butyl ether.

The compounds listed in Table 1 can be prepared similarly to Examples 1 and 3.

The compounds listed in Table 2 can be prepared similarly to Example 2.

TABLE 1

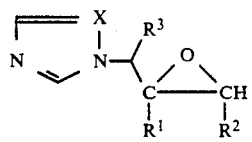

| Ex. | R$^1$ | R$^2$ | R$^3$ | X | m.p./IR | Comment |
|---|---|---|---|---|---|---|
| 1 | 4-F—C$_6$H$_4$ | 2-Cl—C$_6$H$_4$ | Cl | N | 152–156° C. | enantiomer mixture |
| 2 | 4-F—C$_6$H$_4$ | 2-Cl—C$_6$H$_4$ | Cl | CH | 144–152° C. | 1:1 diastereomer mixture |
| 3 | 4-F—C$_6$H$_4$ | 2-Cl—C$_6$H$_4$ | Br | N | 151–155° C. | enantiomer mixture |
| 4 | 4-F—C$_6$H$_4$ | 2-Cl—C$_6$H$_4$ | Br | CH | | |
| 5 | 4-F—C$_6$H$_4$ | 2-Cl—C$_6$H$_4$ | F | N | | |
| 6 | 4-F—C$_6$H$_4$ | 2-Cl—C$_6$H$_4$ | F | CH | | |
| 7 | 4-F—C$_6$H$_4$ | 4-Cl—C$_6$H$_4$ | F | N | | |
| 8 | 4-F—C$_6$H$_4$ | 4-Cl—C$_6$H$_4$ | Cl | N | | |
| 9 | 4-F—C$_6$H$_4$ | 4-Cl—C$_6$H$_4$ | Cl | CH | | |
| 10 | 4-F—C$_6$H$_4$ | 4-Cl—C$_6$H$_4$ | Br | N | | |
| 11 | 4-F—C$_6$H$_4$ | 2,4-Cl$_2$—C$_6$H$_3$ | F | N | | |
| 12 | 4-F—C$_6$H$_4$ | 2,4-Cl$_2$—C$_6$H$_3$ | Cl | N | | |
| 13 | 4-F—C$_6$H$_4$ | 2,4-Cl$_2$—C$_6$H$_3$ | Br | N | | |
| 14 | 4-F—C$_6$H$_4$ | 2-Cl-4-F—C$_6$H$_3$ | F | N | | |
| 15 | 4-F—C$_6$H$_4$ | 2-Cl-4-F—C$_6$H$_3$ | Cl | N | | |
| 16 | 4-F—C$_6$H$_4$ | 2-Cl-4-F—C$_6$H$_3$ | Br | N | | |
| 17 | 4-F—C$_6$H$_4$ | 2-CF$_3$—C$_6$H$_4$ | F | N | | |
| 18 | 4-F—C$_6$H$_4$ | 2-CF$_3$—C$_6$H$_4$ | Cl | N | 126–127° C. | enantiomer mixture |
| 19 | 4-F—C$_6$H$_4$ | 2-CF$_3$—C$_6$H$_4$ | Br | N | | |
| 20 | 4-F—C$_6$H$_4$ | 4-CF$_3$—C$_6$H$_4$ | Cl | N | | |
| 21 | 4-F—C$_6$H$_4$ | 2-F—C$_6$H$_4$ | F | N | | |
| 22 | 4-F—C$_6$H$_4$ | 2-F—C$_6$H$_4$ | Cl | N | | |
| 23 | 4-F—C$_6$H$_4$ | 2-F—C$_6$H$_4$ | Br | N | | |
| 24 | 4-F—C$_6$H$_4$ | 4-F—C$_6$H$_4$ | Cl | N | | |
| 25 | 4-F—C$_6$H$_4$ | 2,4-F$_2$—C$_6$H$_3$ | Cl | N | resin | 1:1 diastereomer mixture |
| 26 | 4-F—C$_6$H$_4$ | 2,4-F$_2$—C$_6$H$_3$ | Cl | CH | 118–123° C. | 1:1 diastereomer mixture |
| 27 | 4-F—C$_6$H$_4$ | 2-OCH$_3$—C$_6$H$_4$ | F | N | | |
| 28 | 4-F—C$_6$H$_4$ | 2-OCH$_3$—C$_6$H$_4$ | Cl | N | 118–124° C. | enantiomer mixture |
| 29 | 4-F—C$_6$H$_4$ | 2-OCH$_3$—C$_6$H$_4$ | Br | N | | |
| 30 | 4-F—C$_6$H$_4$ | ![phenyl] | Cl | N | | |
| 31 | 4-F—C$_6$H$_4$ | 4-NO$_2$—C$_6$H$_4$ | Cl | N | | |
| 32 | 4-F—C$_6$H$_4$ | 4-NH$_2$—C$_6$H$_4$ | Cl | N | | |
| 33 | 4-F—C$_6$H$_4$ | 2-C$_{10}$H$_7$ | F | N | | |
| 34 | 4-F—C$_6$H$_4$ | 2-C$_{10}$H$_7$ | Cl | N | | |
| 35 | 4-F—C$_6$H$_4$ | 2-C$_{10}$H$_7$ | Br | N | | |
| 36 | 4-F—C$_6$H$_4$ | cyclopropyl | Cl | N | | |
| 37 | 4-F—C$_6$H$_4$ | cyclohexyl | Cl | N | | |
| 38 | C$_6$H$_5$ | 2-Cl—C$_6$H$_4$ | Cl | N | | |
| 39 | C$_6$H$_5$ | 2-Cl—C$_6$H$_4$ | Cl | CH | | |
| 40 | C$_6$H$_5$ | 4-Cl—C$_6$H$_4$ | Cl | N | 136–138° C. | enantiomer mixture |
| 41 | C$_6$H$_5$ | 4-Cl—C$_6$H$_4$ | Cl | CH | 167–172 | 1:1 diastereomer mixture |
| 42 | C$_6$H$_5$ | 4-Cl—C$_6$H$_4$ | Br | N | | |
| 43 | C$_6$H$_5$ | 4-Cl—C$_6$H$_4$ | Br | CH | | |
| 44 | C$_6$H$_5$ | 2,4-Cl$_2$—C$_6$H$_3$ | Cl | N | | |
| 45 | C$_6$H$_5$ | 2-F—C$_6$H$_3$ | Cl | N | | |
| 46 | C$_6$H$_5$ | 4-F—C$_6$H$_4$ | Cl | N | | |
| 47 | C$_6$H$_5$ | 2-CF$_3$—C$_6$H$_4$ | Br | N | | |
| 48 | C$_6$H$_5$ | 4-CF$_3$—C$_6$H$_4$ | Cl | N | | |
| 49 | C$_6$H$_5$ | 2-OCH$_3$—C$_6$H$_4$ | Cl | N | | |
| 50 | C$_6$H$_5$ | cyclohexyl | Cl | N | | |
| 51 | 2-Cl—C$_6$H$_4$ | 2-Cl—C$_6$H$_4$ | Cl | N | | |
| 52 | 2-Cl—C$_6$H$_4$ | 4-Cl—C$_6$H$_4$ | Cl | N | | |
| 53 | 4-Cl—C$_6$H$_4$ | 2-Cl—C$_6$H$_4$ | Cl | N | | |
| 54 | 4-Cl—C$_6$H$_4$ | 2-Cl—C$_6$H$_4$ | Br | N | | |
| 55 | 4-Cl—C$_6$H$_4$ | 4-Cl—C$_6$H$_4$ | Cl | N | | |
| 56 | 4-Cl—C$_6$H$_4$ | 2-F—C$_6$H$_4$ | Cl | N | | |
| 57 | 4-Cl—C$_6$H$_4$ | 4-F—C$_6$H$_4$ | Cl | N | | |
| 58 | 4-Cl—C$_6$H$_4$ | 2-CF$_3$—C$_6$H$_4$ | Cl | N | | |
| 59 | 2,4-Cl$_2$—C$_6$H$_3$ | 2-Cl—C$_6$H$_4$ | Cl | N | | |
| 60 | 2,4-Cl$_2$—C$_6$H$_3$ | 2,4-Cl$_2$—C$_6$H$_3$ | Cl | N | | |
| 61 | 4-Br—C$_6$H$_4$ | 2-Cl—C$_6$H$_4$ | Cl | N | | |
| 62 | cyclohexyl | 2-Cl—C$_6$H$_4$ | Cl | N | | |

TABLE 1-continued

| Ex. | R¹ | R² | R³ | X | m.p./IR | Comment |
|---|---|---|---|---|---|---|
| 63 | cyclohexyl | 4-Cl—C₆H₄ | Cl | N | | |
| 64 | cyclohexyl | 2-F—C₆H₄ | Cl | N | | |
| 65 | cyclohexyl | 4-F—C₆H₄ | Cl | N | | |
| 66 | cyclohexyl | 4-F—C₆H₄ | Cl | CH | | |
| 67 | cyclohexyl | 2,4-Cl₂—C₆H₃ | Cl | N | | |
| 68 | cyclohexyl | cyclohexyl | Cl | N | | |
| 69 | tetrahydropyranyl | 2-Cl—C₆H₄ | Cl | N | | |
| 70 | tetrahydropyranyl | 4-Cl—C₆H₄ | Cl | N | | |
| 71 | tetrahydropyranyl | 4-F—C₆H₄ | Cl | N | | |
| 72 | CH₃ | 2-Cl—C₆H₄ | Cl | N | | |
| 73 | CH₃ | 4-F—C₆H₄ | Cl | N | | |
| 74 | 4-F—C₆H₉ | 3-F—C₆H₄ | Cl | N | resin | 2:1 diastereomer mixture |
| 75 | 4-F—C₆H₄ | 4-CF₃—C₆H₄ | Cl | CH | 90-94° C. | 2:1 diastereomer mixture |
| 76 | 4-F—C₆H₄ | 2-Br—C₆H₄ | Cl | N | 151-158° C. | enantiomer mixture |
| 77 | 4-F—C₆H₄ | 2-Br—C₆H₄ | Cl | CH | 159-164° C. | enantiomer mixture |
| 78 | 4-F—C₆H₄ | C₆H₅ | Cl | N | 134-138° C. | 12:1 diastereomer mixture |
| 79 | 4-F—C₆H₄ | C₆H₅ | Cl | CH | resin | 1:1 diastereomer mixture |
| 80 | C₆H₅ | 2,4-Cl₂—C₆H₃ | Cl | CH | 176-180° C. | enantiomer mixture |

TABLE 2

| Ex. | R¹ | R² | R³ | X | m.p./IR (cm⁻¹) | Isomer |
|---|---|---|---|---|---|---|
| 1a | 4-F—C₆H₄ | 2-Cl—C₆H₄ | Cl | N | 1509,1276,1134,1015,849,806,752 | E |
| 2a | 4-F—C₆H₄ | 2-Cl—C₆H₄ | Cl | CH | | |
| 3a | 4-F—C₆H₄ | 2-Cl—C₆H₄ | Br | N | | |
| 4a | 4-F—C₆H₄ | 2-Cl—C₆H₄ | Br | CH | | |
| 5a | 4-F—C₆H₄ | 2-Cl—C₆H₄ | F | N | | |
| 6a | 4-F—C₆H₄ | 2-Cl—C₆H₄ | F | CH | | |
| 7a | 4-F—C₆H₄ | 4-Cl—C₆H₄ | Cl | N | | |
| 8a | 4-F—C₆H₄ | 4-Cl—C₆H₄ | Cl | CH | | |
| 9a | 4-F—C₆H₄ | 4-Cl—C₆H₄ | Br | N | | |
| 10a | 4-F—C₆H₄ | 2,4-Cl₂—C₆H₃ | Cl | N | | |
| 11a | 4-F—C₆H₄ | 2,4-Cl₂—C₆H₃ | Br | N | | |
| 12a | 4-F—C₆H₄ | 2-Cl-4-F—C₆H₃ | Cl | N | | |
| 13a | 4-F—C₆H₄ | 2-Cl-4-F—C₆H₃ | Br | N | | |
| 14a | 4-F—C₆H₄ | 2-CF₃—C₆H₄ | Cl | N | 1509,1315,1170,1124,1035,848,769 | E/Z = 7:3 |
| 15a | 4-F—C₆H₄ | 2-CF₃—C₆H₄ | Cl | CH | | |
| 16a | 4-F—C₆H₄ | 2-CF₃—C₆H₄ | Br | N | | |
| 17a | 4-F—C₆H₄ | 4-CF₃—C₆H₄ | Cl | N | | |
| 18a | 4-F—C₆H₄ | 4-CF₃—C₆H₄ | Br | N | | |
| 19a | 4-F—C₆H₄ | 2-F—C₆H₄ | Cl | N | | |
| 20a | 4-F—C₆H₄ | 2-F—C₆H₄ | Cl | CH | | |
| 21a | 4-F—C₆H₄ | 2-F—C₆H₄ | Br | N | | |
| 22a | 4-F—C₆H₄ | 2,4-F₂—C₆H₃ | Cl | N | | |
| 23a | 4-F—C₆H₄ | 2-OCH₃—C₆H₄ | Cl | N | | |
| 24a | 4-F—C₆H₄ | 2-OCH₃—C₆H₄ | Cl | N | | |

TABLE 2-continued $$\underset{R^2}{\overset{}{\underset{}{\bigg\rvert}}}\text{N}\underset{}{\overset{}{\diagdown}}\text{N}\underset{}{\overset{X}{\underset{|}{\diagup}}}\underset{CH-R^2}{\overset{R^3}{\diagup}}$$

| Ex. | $R^1$ | $R^2$ | $R^3$ | X | m.p./IR (cm$^{-1}$) | Isomer |
|---|---|---|---|---|---|---|
| 25a | 4-F—$C_6H_4$ | (4-substituted phenyl) | Cl | N | | |
| 26a | 4-F—$C_6H_4$ | 2-$C_{10}H_7$ | Cl | CH | | |
| 27a | 4-F—$C_6H_4$ | 2-$C_{10}H_7$ | Br | N | | |
| 28a | 4-F—$C_6H_4$ | cyclohexyl | Cl | N | | |
| 29a | 4-F—$C_6H_4$ | cyclohexyl | Br | N | | |
| 30a | $C_6H_5$ | 2-Cl—$C_6H_4$ | Cl | N | | |
| 31a | $C_6H_5$ | 2-Cl—$C_6H_4$ | Br | N | | |
| 32a | $C_6H_5$ | 4-Cl—$C_6H_4$ | F | N | | |
| 33a | $C_6H_5$ | 4-Cl—$C_6H_4$ | Cl | N | | |
| 34a | $C_6H_5$ | 4-Cl—$C_6H_4$ | Cl | CH | | |
| 35a | $C_6H_5$ | 4-Cl—$C_6H_4$ | Br | N | | |
| 36a | $C_6H_5$ | 2-F—$C_6H_4$ | Cl | N | | |
| 37a | $C_6H_5$ | 4-F—$C_6H_4$ | Cl | N | | |
| 38a | $C_6H_5$ | 2-$CF_3$—$C_6H_4$ | Cl | N | | |
| 39a | $C_6H_5$ | 4-$CF_3$—$C_6H_4$ | Cl | N | | |
| 40a | $C_6H_5$ | cyclohexyl | Cl | N | | |
| 41a | 4-Cl—$C_6H_4$ | 2-Cl—$C_6H_4$ | Cl | N | | |
| 42a | 4-Cl—$C_6H_4$ | 2-Cl—$C_6H_4$ | Cl | CH | | |
| 43a | 4-Cl—$C_6H_4$ | 4-Cl—$C_6H_4$ | Cl | N | | |
| 44a | 4-Cl—$C_6H_4$ | 4-Cl—$C_6H_4$ | Br | N | | |
| 45a | 2,4-$Cl_2$—$C_6H_3$ | 2-Cl—$C_6H_4$ | Cl | N | | |
| 46a | 2,4-$Cl_2$—$C_6H_3$ | 2,4-$Cl_2$—$C_6H_3$ | Cl | N | | |
| 47a | cyclohexyl | 2-Cl—$C_6H_4$ | Cl | N | | |
| 48a | cyclohexyl | 2,4-$Cl_2$—$C_6H_3$ | Cl | N | | |
| 49a | cyclohexyl | 2-F—$C_6H_4$ | Cl | N | | |
| 50a | cyclohexyl | 4-F—$C_6H_4$ | Cl | N | | |
| 51a | (tetrahydropyranyl) | 2-Cl—$C_6H_4$ | Cl | N | | |
| 52a | (tetrahydropyranyl) | 2-Cl—$C_6H_4$ | Br | N | | |
| 53a | $CH_3$ | 4-F—$C_6H_4$ | Cl | N | | |

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminis in cereals.
Erysiphe cichoracearum and Sphaerotheca fuliginea in cucurbits.
Podosphaera leucotricha in apples,
Uncinula necator in vines.
Puccinia species in cereals,
Rhizoctonia species in cotton and lawns.
Ustilago species in cereals and sugar cane,
Venturia inaequalis (scab) in apples,
Helminthosporium species in cereals,
Septoria nodorum in wheat,
Botrytis cinerea (gray mold) in strawberries and grapes.
Cercospora arachidicola in qroundnuts,
Pseudocercosporella herpotrichoides in wheat and barley.
Pyricularia oryzae in rice.
Phytophthora infestans in potatoes and tomatoes,
Fusarium and Verticillium species in various plants,
Plasmopara viticola in grapes.
Alternaria species in fruit and vegetables.

The compounds are applied by spraying or dusting the plants with the active ingredients, or treating the seeds of the Plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene, chlorinated aromatics (e.g., chlorobenzenes). paraffins e.g.. crude oil fractions), alcohols e.g.. methanol, butanol, ketones (e.g., cyclohexanone), amines e.g.. ethanolamine. dimethylformamide, and water; carriers such as ground natural minerals e.g., kaolins. aluminas talc and chalk and ground synthetic minerals e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90 wt. of active ingredient. The application rates are from 0.02 to 3 kg or more of active ingredient per hectare, depending on the type of effect desired. The novel compounds may also be used for protecting materials, for example against Paecilomyces variotii.

The agents and the ready-to-use formulations prepared from them, such as solutions, emulsions, susPensions, powders, dusts, pastes and granules, are applied in conventional manner, for example by spraying, atomizing, dusting, scattering, dressing or watering.

Examples of formulations are given below.

I. 90 parts by weight of compound no. 40 is mixed with 10 parts by weight of N-methyl-α-pyrrolidone. A mixture is obtained which is suitable for application in the form of very fine drops.

II. 20 parts by weight of compound no. 41 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein an aqueous dispersion is obtained.

III. 20 parts by weight of compound no. 40 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 41 is dissolved in a mixture consisting of 25 parts by weight of cyclohexanol, 65 parts by weight of a mineral oil fraction having a boiling point between 210° and 280° C. and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 40 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 41 is intimately mixed with 97 parts by weight of particulate kaolin. A dust is obtained containing 3% by weight of the active ingredient.

VII. 30 parts by weight of compound no. 40 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 41 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 40 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides insecticides, growth regulators, and fungicides, and may furthermore be mixed and applied together with fertilizers. Admixture with other fungicides frequently results in an increase in the fungicidal spectrum.

The following list of fungicides with which the novel compounds may be combined is intended to illustrate possible combinations but not to impose any restrictions.

Examples of fungicides which may be combined with the novel compounds are:
sulfur.
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate
tetramethylthiuram disulfides,
ammonia complex of zinc N,N'-ethylenebisdithiocarbamate
ammonia complex of zinc N,N'-propylenebisdithiocarbamate,
zinc N,N'-propylenebisdithiocarbamate and
N,N'-polypropylenebisthiocarbamyl) disulfide;
nitro derivatives, such as
dinitro(1-methylheptyl-phenyl crotonate,
2-sec-butyl-4,6-dinitrophenyl 3,3-dimethylacrylate.
2-sec-butyl-4,6-dinitrophenyl isopropylcarbonate and
20 diisopropyl 5-nitroisophthalate;
heterocyclic substances, such as
2-heptadecylimidazol-2-yl acetate.
2,4-dichloro-6-(o-chloroanilino)-s-triazine,
0,0-diethyl phthalimidophosphonothioate,
5-amino-1-[-bis-(dimethylamino)-phosphinyl]-3-phenyl-1,2,4-triazole,
2.3-dicyano-1,4-dithioanthraquinone.

2-thio-1,3-dithio[4,5-b]quinoxaline.
methyl 1-(butylcarbamyl)-2-benzimidazolecarbamate,
2-methoxycarbonylaminobenzimidazole.
2-fur-2-yl-benzimidazole.
2-(thiazol-4-yl)benzimidazole,
N-1,1,2,2-tetrachloroethyithio)-tetrahydrophthalimide.
N-trichloromethylthiotetrahydrophthalimide
N-trichloromethylthiophthalimide,
N-dichlorofluoromethylthio-N',N'-dimethyl-N-phenyl-sulfuric acid diamide.
5-ethoxy-3-trichloromethyl-1,2,3-thiadiazole,
2-thiocyanatomethylthiobenzothiazole,
1,4-dichloro-2,5-dimethoxybenzene,
4-2-chlorophenylhydrazono-3-methyl-5-isoxazolone.
2-thiopyridine 1-oxide.
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methylfuran-3-carboxanillde,
3 2,5-dimethylfuran-3-carboxanilide.
2,4,5-trlmethylfuran-3-carboxanilide,
2,5-dimethyl-N-cyclohexylfuran-3-carboxamlde.
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal.
piperazine-1,4-diylbis-(1-(2,2,2-trichloroethyl-formamide),
1-3,4-dichloroanilino)-l-formylamino-2,2,2-trichloroethane,
2,6-dimethyl-N-tridecylmorpholine and its salts
2,6-dimethyl-N-cyclododecylmorpholine and its salts,
N-13-p-tert.-butylphenyl-2-methylpropyl]-cis-2,6-dimethylmorpholine,
N-3-p-tert.-butylphenyl)-2-methylpropyl]-piperidine,
1-[2-(2,4-dichlorophenyl)-4-ethyl-1,3-dioxolan-2-ylmethyl]-1H-1,2,4-triazole,
1-[2-(2,4-dichlorophenyl)-4-n-propyl-1,3-dioxolan-2-ylethyl]-1H-1,2,4-triazole,
N-n-propyl-N-2,4,6-trichlorophenoxyethyl-N'-imidazolyl-urea,
1-(4-chlorophenoxy)-3,3-dimethyl-1-1H-1,2,4-triazol-1-yl-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-p-chlorophenyl)-3-pyridinemethanol,
1,2-bis-3-ethoxycarbonyl-2-thioureido-benzene,
1,2-bis-3-methoxycarbonyl -2-thioureido)-benzene, and various fungicides, such as dodecylguanidine acetate,
3-[3-3,5-dimethyl-2-oxycyclohexyl-2-hydroxyethyl]-glutaramide, hexachlorohenzene,
DL-methyl-N-(2,6-dimethylphenyl)-N-fur-2-yl alanate,
methyl DL-N-2,6-dimethylphenyl-N-(2'-methoxyacetyl-alanate.
N-(2,6-dimethylphenyl)-N-chloroacetyl-DL-2-aminobutyrolactone,
methyl DL-N-2,6-dimethylphenyl)-N-phenylacetyl-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3.5-dichlorophenyl)-1,2-dimethylcyclopropane-1,2-dicarboximide
2cyano-[N-(ethylaminocarbonyl)-2-methoximino]-acetamide,
1-[2-(2,4-dichlorophenyl)-pentyl]-1H-1,2,4-triazole,
2,4-difluoro-α-1H-1,2,4-triazol-1-ylmethyl-benzhydryl alcohol.
N-3-chloro-Z,6-dinitro-4-trifluoromethylphenyl)-5-trifluoromethyl-3-chloro-2-aminopyridine, and
1-((bis-(4-fluorophenyl-methylsilyl)-methyl)-1H-1,2,4-triazole.

Use example

The active ingredients 2-(1,2,4-triazol-1-yl-methyl)-2-phenyl-3-(4-chlorophenyl)-oxirane (A) and 2-(imidazol-1-yl-methyl)-2-phenyl-3-(4-chlorophenyl-oxirane (B) disclosed in DE 3,218,130 were used for comparison purposes Action on wheat mildew Leaves of pot-grown wheat seedlings of the "Kanzler" variety were sprayed with aqueous liquors containing dry basis 80T of active ingredient and 20% of emulsifier, and dusted, 24 hours after the sprayed-on layer had dried, with spores of wheat mildew (Erisyphe graminis var. tritici). The plants were then set up in the greenhouse at 20° to 22° C. and a relative humidity of 75 to 80%. The extent of fungus spread was assessed after 7 days.

The results show that active ingredients 40 and 41, when applied as 0.025wt% spray liquors, had a better fungicidal action (95%) than prior art active ingredients A and B (80%).

We claim:

1. A compound of the formula I

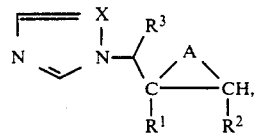

where $R^1$ and $R^2$ are identical or different and each is $C_5$–$C_8$-cycloalkyl, $C_5$–$C_8$-cycloalkenyl, tetrahydropyranyl or norbornyl, each of these radicals being unsubstituted or mono- to trisubstituted by halogen, nitro, phenoxy, amino, alkyl, alkoxy or haloalkyl, each of 1 to 4 carbon atoms, A is oxygen, $R^3$ is F, Cl or Br, X is N, or their plant-tolerated acid addition salts or metal complexes.

2. A compound of the formula:

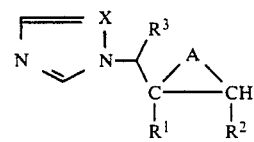

wherein X is nitrogen, A is oxygen, $R^1$ is phenyl, $R^2$ is 4-chlorophenyl and $R^3$ is chloro; or a plant tolerated acid addition salt or metal complex thereof.

3. A fungicidal composition containing a carrier and a fungicidally effective amount of a compound of claim 1.

4. A fungicidal composition containing a carrier and a fungicidally effective amount of a compound of claim 2.

5. A process for combatting fungi, wherein a fungicidally effective amount of a compound of claim 1 is allowed to act on the fungi, or plant materials, areas in which plants are located, plants or seed threatened by fungus attack.

6. A process for combatting fungi, wherein a fungicidally effective amount of a compound of claim 2 is allowed to act on the fungi, or plant materials, areas in which plants are located, plants or seed threatened by fungus attack.

* * * * *